US00PP29337P3

(12) United States Plant Patent
Schoone

(10) Patent No.: US PP29,337 P3
(45) Date of Patent: May 29, 2018

(54) ***PHALAENOPSIS* ORCHID PLANT NAMED 'KISSY LIPS'**

(50) Latin Name: *Phalaenopsis hybrida*
Varietal Denomination: Kissy Lips

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days. days.

(21) Appl. No.: 15/330,463

(22) Filed: Sep. 23, 2016

(65) Prior Publication Data

US 2017/0094872 P1 Mar. 30, 2017

Related U.S. Application Data

(60) Provisional application No. 62/222,896, filed on Sep. 24, 2015.

(51) Int. Cl.
*A01H 5/02* (2018.01)

(52) U.S. Cl.
USPC ..... Plt./311

(58) Field of Classification Search
USPC ..... Plt./311
CPC ..... A01H 5/02; A01H 5/00
See application file for complete search history.

(56) References Cited

U.S. PATENT DOCUMENTS

PP25,776 P3 * 8/2015 Schoone ..... A01H 5/02
Plt./311

* cited by examiner

*Primary Examiner* — June Hwu
(74) *Attorney, Agent, or Firm* — Sunit Talapatra; Foley & Lardner LLP

(57) ABSTRACT

A new and distinct *Phalaenopsis* plant named 'Kissy Lips' particularly characterized by flowers which are purple with a darker purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Kissy Lips'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Kissy Lips'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Kissy Lips' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Kissy Lips' originated from a cross made by the inventor in 2003 in Strengweg, Heemskerk, The Netherlands. The female or seed parent is the *Phalaenopsis* cultivar designated 'Sogo Tical', unpatented. The male or pollen parent is the *Phalaenopsis* cultivar designated 'Sogo Berry', unpatented. The new *Phalaenopsis* 'Kissy Lips' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in July, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Kissy Lips', which in combination distinguish this *Phalaenopsis* as a new and distinct cultivar:

1. flowers which are purple with a darker purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Kissy Lips', the flowers of the female parent 'Sogo Tical' are purple but a little larger than 'Kissy Lips', the flowers of the male parent 'Sogo Berry' are purple but a little smaller than 'Kissy Lips'.

Presently, the commercial cultivar to which 'Kissy Lips' can be meaningfully compared is 'Lions Dive' (U.S. Plant Pat. No. 25,776). 'Kissy Lips' has purple flowers and labellum, whereas 'Lions Dive' has purple/violet flowers and labellum. 'Lions Dive' is also about 50 cm in size, whereas 'Kissy Lips' is about 40 cm in size.

BRIEF DESCRIPTION OF THE PHOTOGRAPHS

The accompanying photographs illustrate the overall appearance of the new *Phalaenopsis* 'Kissy Lips' showing the colors as true as is reasonably possible with colored reproductions of this type. Colors in the photographs may differ slightly from the color values cited in the detailed botanical description, which accurately describe the color of 'Kissy Lips'.

DETAILED BOTANICAL DESCRIPTION

Figure 1:
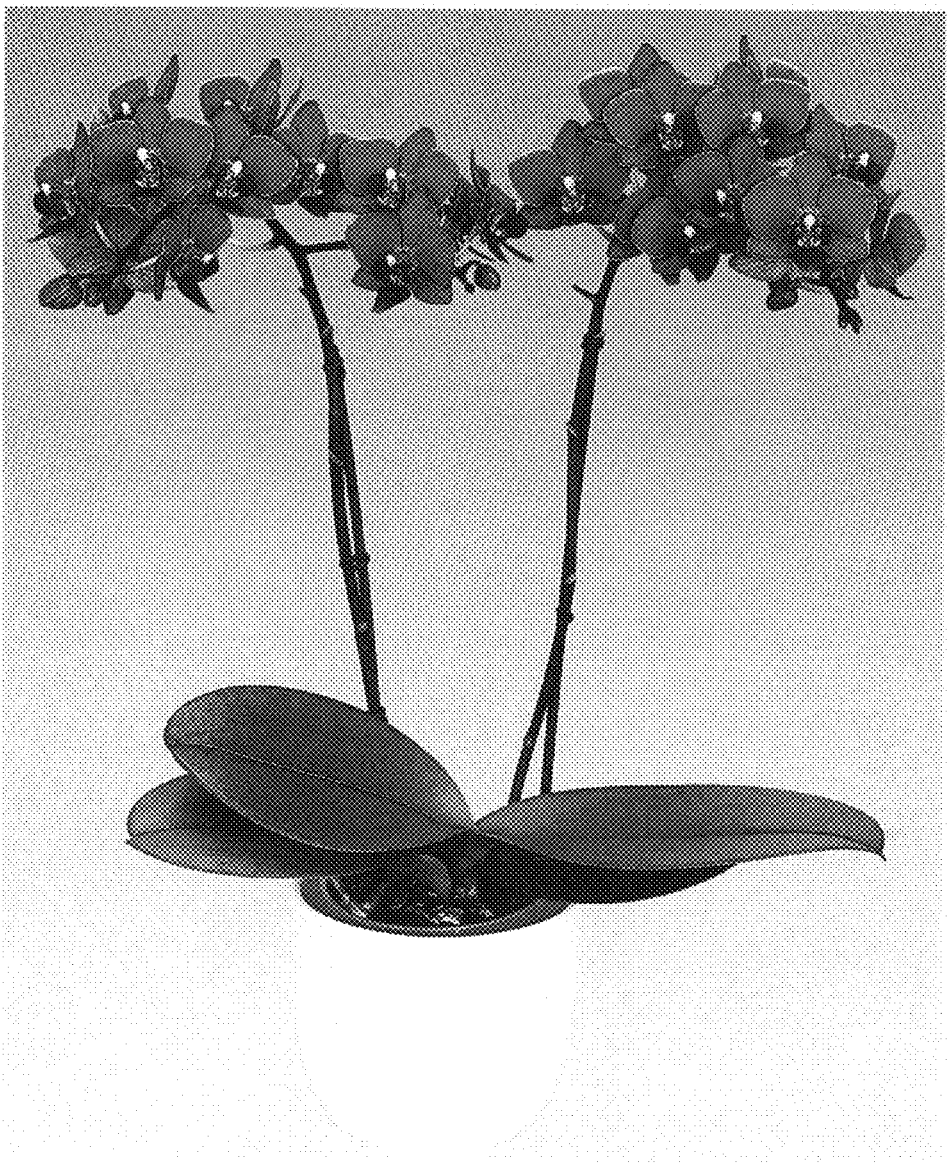
FIG. 1 shows a side view perspective of a typical flowering plant of 'Kissy Lips' in a 12 cm pot, at 16 months of age.

The new *Phalaenopsis* cultivar 'Kissy Lips' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Kissy Lips' as grown in a greenhouse in Strengweg, Heemskerk, The Netherlands, under conditions which closely approximate those generally used in commercial practice. Initially, the ideal temperature to grow plants of 'Kissy Lips' is 27° C. during the day and at night. Then, during the flowering phase of 'Kissy Lips', the ideal growing temperature is 20-22° C. during the day and 18° C. at night. Light levels for growing 'Kissy Lips' are a minimum of 5,000 lux and a maximum of 10,000 lux. A balanced fertilizer with level of 200 ppm N, 87 ppm P, 168 ppm K is applied. Duration of growth of 'Kissy Lips' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Kissy Lips' plants described is 12 months after potting.

Classification:

*Botanical.—Phalaenopsis hybrida.*

Parentage:

*Female or seed parent.—Phalaenopsis* cultivar designated 'Sogo Tical', unpatented.

*Male or pollen parent.—Phalaenopsis* cultivar designated 'Sogo Berry', unpatented.

Propagation:

*Type.*—Tissue culture.

*Rooting habit and description.*—Fleshy; approximately 5 mm-7 mm wide and greyed/green in color (RHS 190B); freely branching. It takes 12 weeks for plants growing in tissue culture to initiate roots.

Plant:

*Size at maturity.*—Height (from bottom of pot to highest flower): about 40 cm. Spread: about 40 to 50 cm.

*Growth habit.*—Small; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6-8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None.

*Mature leaf length.*—About 16 cm.

*Mature leaf width.*—About 8 cm.

*Mature leaf thickness.*—About 2 mm.

*Mature leaf color.*—Upper side: green (RHS N137A). Under side: green (RHS 137B).

*Leaf base.*—Acute.

*Margin.*—Entire.

*Venation.*—Pattern: parallel. Color of midvein: upper side: green (RHS 139A). Under side: green (RHS 139A).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 3.

*Number of flowers per raceme.*—About 13-25.

*Length.*—About 12 cm.

*Diameter.*—About 10 cm.

Peduncle:

*Length.*—About 40 cm.

*Diameter.*—About 6 mm.

*Strength.*—Strong.

*Aspect.*—Upright.

*Texture.*—Glabrous and smooth.

*Color.*—Yellow/green (RHS 146A and RHS 146B) with brown (RHS N200A).

Buds:

*Height* (*from base to tip*).—About 12-15 mm.

*Diameter* (*at midpoint*).—About 7-15 mm.

*Shape*.—Asymmetric oval.

*Color*.—Purple (RHS N79C) with some yellow/green (RHS 144B).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
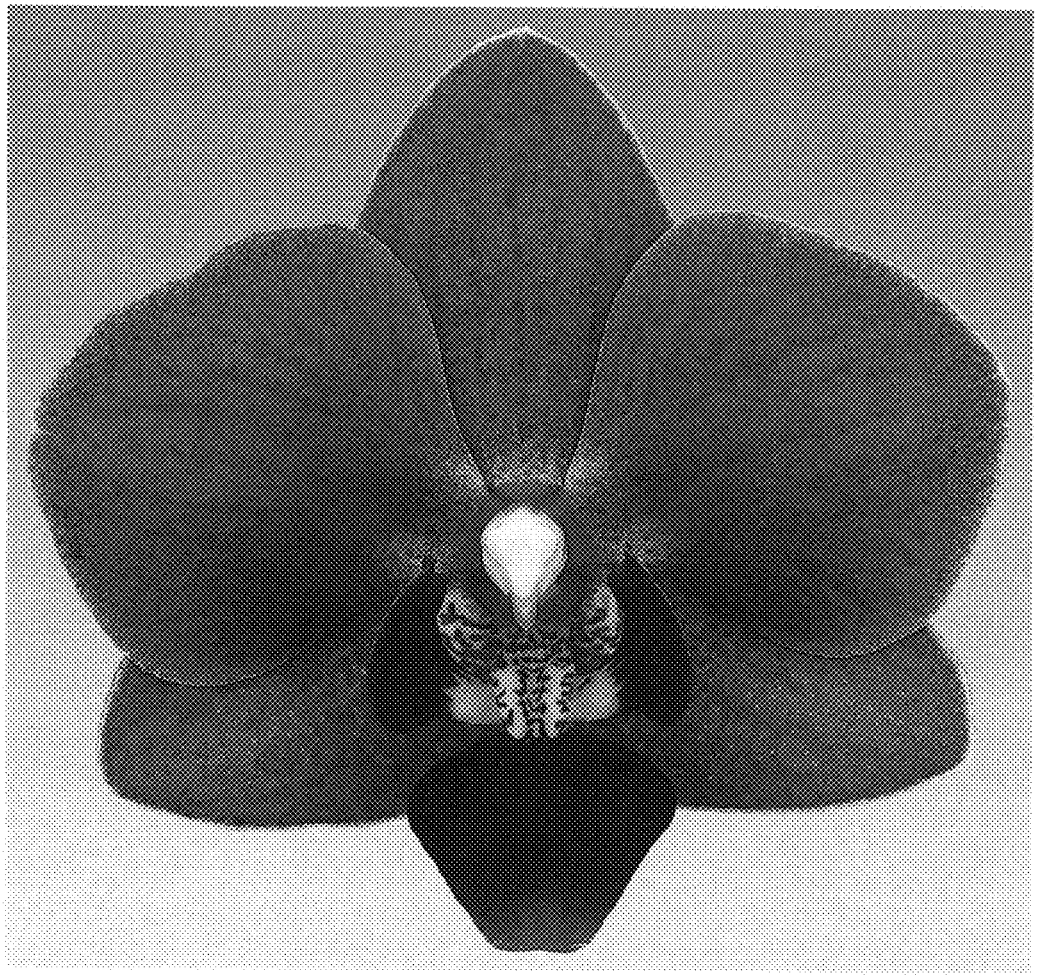
FIG. 2 shows a close-up view of the typical flower of 'Kissy Lips'.
Figure 3:
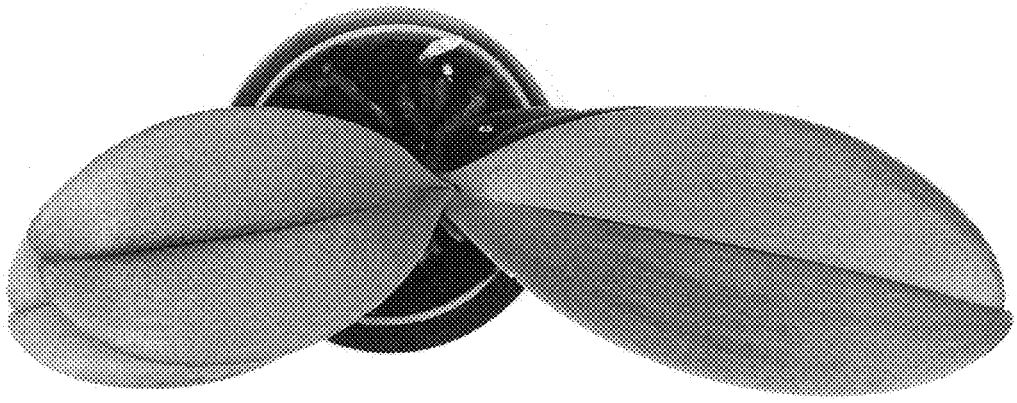
FIG. 3 shows a close-up view of the typical leaves of 'Kissy Lips'.

*Shape*.—Typical shape of *Phalaenopsis*; see FIG. 2.

*Size* (*of single bloom*).—Height: about 42 mm. Diameter: about 49 mm.

*Quantity and arrangement*.—Three petals and three sepals; arrangement of petals are free, not touching. Petals are more pronounced than sepals.

Petals:

*Arrangement*.—Inner whorl comprises 3 petals: 2 lateral petals and a labellum.

2 *lateral petals*.—Overall shape: little triangular and weakly cupped. Apex: oval. Margin: entire and weakly undulate. Base: broadly ovate. Length: about 22 mm. Width: about 25 mm. Texture: Upper surface: smooth and satiny. Under surface: smooth and satiny. Color (when fully opened): upper side: main color is purple (RHS N78A) with a red/purple haze (RHS 70B). At the edges some white (RHS NN155D). At the base some white (RHS NN155D) and red/purple (RHS 70B) with red/purple stripes and spots (RHS 72A). Under side: purple (RHS 77B) with some white at the base, the top and on the edges (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire and weakly undulate. Apex of the midlobe and lateral lobes: oval. Length midlobe: about 23 mm. Width midlobe (not flattened): about 15 mm. Length lateral lobe: about 21 mm. Width lateral lobe (not flattened): about 16 mm. Depth of tube created by lateral lobes of labellum: about 21 mm. Texture: Upper & under surface: smooth and satiny. Color (when fully opened): Midlobe, upper side: main color is purple (RHS N79A) with closer to the cirrhi red/purple (RHS 72A). Under side: red/purple (RHS 72A) with on the edges purple (RHS N79A) with some grey/white (RHS 156D). In the center a haze of white (RHS NN155C) Lateral lobes, upper side: at the base white (RHS NN155D) with a yellow haze (RHS 13A) which runs into purple (RHS N79A) and purple (RHS 77A). Under side: at the base white (RHS NN155A) which runs into purple (RHS N79A) and purple (RHS 77A). Cirrhi: about 1 mm. Color: red/purple (RHS 72A). Pestle (Callosities): Length: about 3 mm. Width (not flattened): about 4 mm. Color: main color is yellow (RHS 13A) with red/purple stripes and spots (RHS 59A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 22 mm.

*Width*.—About 17 mm.

*Apex*.—Oval/little pointy.

*Texture*.—Upper and under surface: smooth and satiny.

*Color* (*when fully opened*).—Upper side, dorsal: purple (RHS N78A) with red/purple stripes and spots (RHS 70B) at the edge and base some white (RHS NN155C). Lateral: main color is purple (RHS N78A) with a white haze (RHS N155B). At the base some white (RHS NN155C). From the base some purple spots (RHS 78A) which runs into red/purple spots (RHS 70B). Under side, dorsal: purple (RHS N78C) with a white haze (RHS N155B) Lateral: purple (RHS N78A) with a white haze (RHS N155B) and some red/purple stripes (RHS 70B).

Pedicel:

*Length*.—About 30 mm.

*Diameter*.—About 3 mm.

*Texture*.—Glabrous and smooth.

*Color*.—White (RHS N155B) with purple (RHS 78A) with some yellow/green (RHS 146B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed to date.

Column:

*Length*.—About 10 mm.

*Diameter*.—About 3 mm.

*Color*.—Purple (RHS N78A) with some additional purple (RHS N78D) and white (RHSN155B) at the end.

Pollinia:

*Quantity*.—Two.

*Diameter*.—About 3 mm.

*Color*.—Yellow/orange (RHS 23A).

Ovary:

*Length*.—About 3 mm.

*Diameter*.—About 2 mm.

*Color*.—White (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Kissy Lips', as illustrated and described herein.

* * * * *